United States Patent [19]

Schinzel et al.

[11] 3,996,213

[45] Dec. 7, 1976

[54] 1,2,4-TRIAZOLYL-(1) DERIVATIVES, A PROCESS FOR THEIR PREPARATION AND THEIR USE AS OPTICAL BRIGHTENERS

[75] Inventors: Erich Schinzel; Hans Frischkorn, both of Hofheim, Taunus; Günter Rösch, Altenhain, Taunus, all of Germany

[73] Assignee: Hoechst Aktiengesellschaft, Frankfurt am Main, Germany

[22] Filed: June 2, 1975

[21] Appl. No.: 582,683

[30] Foreign Application Priority Data

June 6, 1974 Switzerland ............... 7749/74

[52] U.S. Cl. .............. 260/240 C; 252/301.22; 252/301.23; 252/301.24; 260/240 CA; 260/240 D; 260/240.9; 260/240.1

[51] Int. Cl.² ............................ C07D 249/09

[58] Field of Search .... 260/240 CA, 240 D, 240 C, 260/240.9, 240.1, 308 R

[56] References Cited

UNITED STATES PATENTS

| | | |
|---|---|---|
| 3,635,960 | 1/1972 | DiGiovanoel et al. ........ 260/240 D |
| 3,679,668 | 7/1972 | Horn et al. ................. 260/240 CA |
| 3,758,462 | 9/1973 | Siegrist et al. ............ 260/240 CA |
| 3,781,278 | 12/1973 | Siegrist et al. ............ 260/240 CA |
| 3,840,528 | 10/1974 | Seino et al. .................. 260/240.9 |

*Primary Examiner*—Arthur P. Demers
*Attorney, Agent, or Firm*—Connolly and Hutz

[57] ABSTRACT

Compounds of the formula

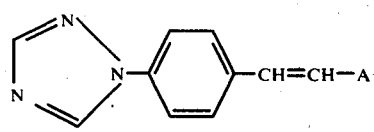

and the corresponding lower alkyl quaternary salts thereof in which A represents a group of the formula

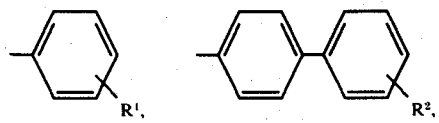

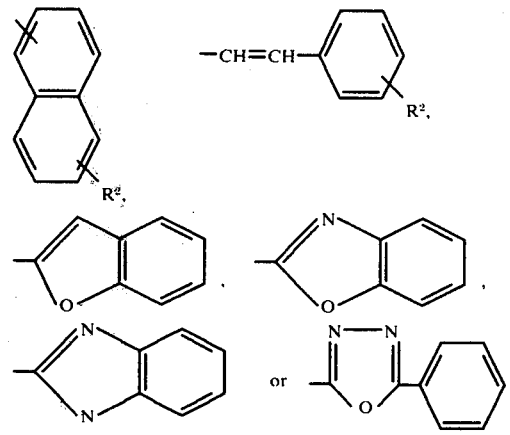

and in which R¹ stands for a group of the formula

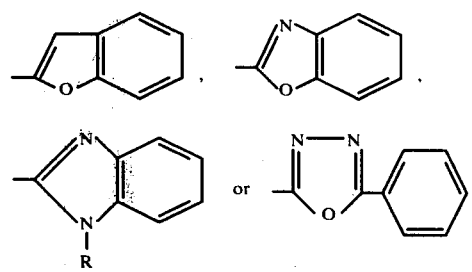

whereby R represents a hydrogen atom or a lower alkyl group, R² has the same meaning as R¹ or stands for a hydrogen atom or a group of the formula

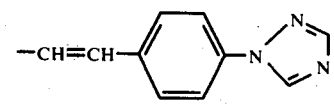

whereby the aromatic rings may be substituted by non-chromophoric substituents. Due to their good fluorescence these compounds can be used as optical brighteners for organic materials, especially textile materials.

6 Claims, No Drawings

1,2,4-TRIAZOLYL-(1) DERIVATIVES, A PROCESS FOR THEIR PREPARATION AND THEIR USE AS OPTICAL BRIGHTENERS

The preparation of 1,2,4-triazolyl-(1)-derivatives of the stilbene- and bis-styryl-benzene series, starting from diamines and nitro-amino- compounds, has been described in U.S. Pat. No. 3,679,668 and their use as optical brighteners was mentioned therein.

The present invention concerns new 1,2,4-triazolyl-(1) derivatives which are colourless or weakly yellow and which show in solution a more or less strong violettish-blue to greenish blue fluorescence, corresponding to the formula (1)

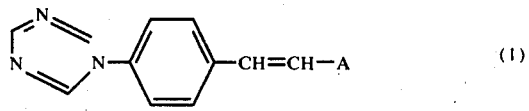

in which A represents a group of the formula

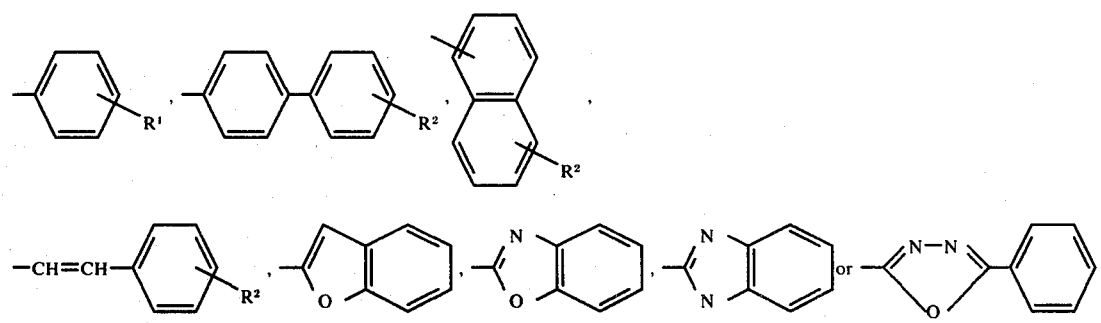

and in which $R^1$ stands for a group of the formula

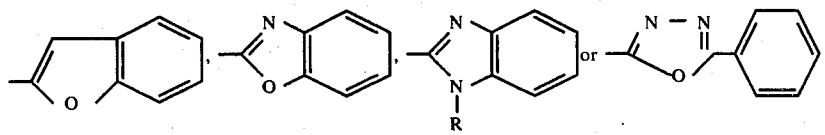

whereby R represents a hydrogen atom or a lower alkyl group, $R^2$ has the same meaning as $R^1$ or stands for a hydrogen atom or a group of the formula

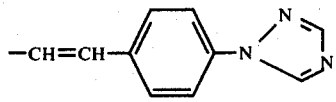

whereby the aromatic rings may be substituted by non-chromophoric substituents, as well as the salts of these compounds with colourless anions.

As non-chromophoric substituents there can be cited, in the first instance: preferably lower alkyl groups, preferably lower alkenyl groups, preferably lower alkoxy groups, aryl radicals, preferably phenyl radicals, aralkyl groups which derive preferably from lower alkylen- and phenyl radicals, such as benzyl- and phenylethyl, acyl-, optionally functionally modified carboxy or sulfo groups, acylamino- or sulfonyl groups as well as halogen atoms. Two lower alkyl radicals may form together an annellated phenyl or cycloalkyl ring.

Functionally modified carboxy groups are generally in the largest sense derivatives of carboxylic acid, i.e. compounds with one carbon atom from which emanate three links to hetero atoms, especially oxygen, nitrogen and sulfur. In a narrower sense they are salts with colourless cations, preferably alkali metal- or ammonium ions, furthermore the group cyano, a carbon ester group or a carboxylic acid amide group. Carboxylic acid ester groups are especially those of the general formula $COOQ^1$, in which $Q^1$ stands for a phenyl radical or an eventually branched lower alkyl group, whereby these radicals can contain further substituents such as, preferably lower dialkylamino-, lower trialkyl-ammonium-, a hydroxy- or a lower alkoxy group. A carboxylic acid amide group is especially a group of the formula $CONQ^2Q^3$ in which $Q^2$ and $Q^3$ represent hydrogen atoms or lower, or eventually substituted alkyl groups which can form together with the nitrogen atom a hydroaromatic ring, acid hydrazides and the analogous thio-derivatives.

Functionally modified sulfo groups are — in analogy to the fore-going — radicals of which the sulfo group is linked with a hetero atom, this means the salts with colourless cations, preferably alkali metal- or ammonium ions, sulfonic acid ester groups and the sulfonamide group. A sulfonic acid ester group is especially a group of the formula $SO_2OQ^1$ in which $Q^1$ has the before-mentioned meaning; a sulfonamide group is a group of the formula $SO_2NQ^2Q^3$ in which $Q^2$ and $Q^3$ have also the before-mentioned meaning.

An acyl group is especially a group of the formula $COQ^4$, in which $Q^4$ stands for an eventually substituted, preferably lower alkyl or phenyl radical, especially for an unsubstituted lower alkanoyl group or for the benzoyl group.

A sulfonyl radical is a radical of the formula $SO_2Q^4$, in which $Q^4$ stands for an eventually substituted lower alkyl or phenyl group, whereby these groups can contain preferably a lower dialkylamino-, a lower trialkylammonium-, an acylamino or a sulfo group as substituent.

Preferred compounds are those in which A represents a group of the formula

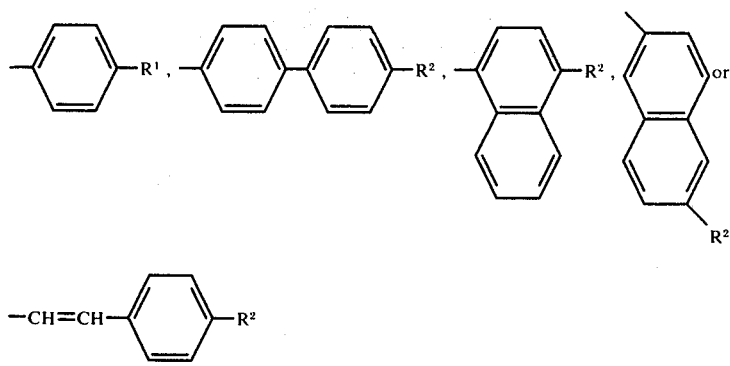

in which R¹ and R² have the signification as given in claim 1, especially the compounds, in which R¹ stands for a group of the formula

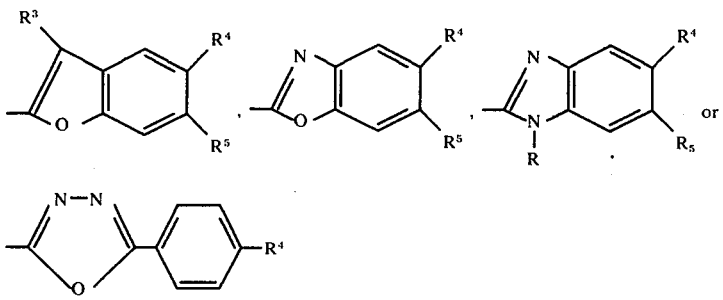

in which R³ represents a hydrogen or a halogen atom or a lower alkyl group, R⁴ and R⁵ hydrogen or halogen atoms, cyano-, lower alkyl and lower alkoxy groups as well as groups of the formulae

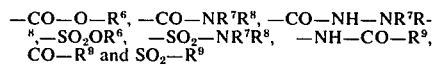

whereby R⁶ stands for a hydrogen atom, a lower alkyl- or a phenyl group which can be substituted by hydroxy-, lower alkoxy, lower dialkylamino- or lower trialkylammonium groups, R⁷ and R⁸ represent hydrogen atoms, lower alkyl groups, which can be substituted by hydroxy-, lower alkoxy-, lower dialkylamino- or lower trialkylammonium groups, or which form together with the nitrogen atom a saturated 5- or 6-membered ring, which can contain a further nitrogen- or oxygen atom, such as the pyrrolidino, piperidino, piperazyl or morpholyl ring, R⁹ has the same signification as R⁶ with the exception of the hydrogen atom, R² has the significations as indicated for R¹ and stands furthermore for a hydrogen atom, a group cyano as well as for groups of the formula

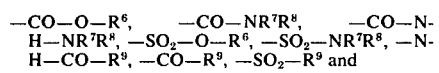

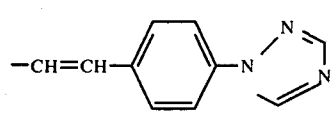

in which R⁶, R⁷, R⁸ and R⁹ have the abovementioned meaning.

It has to be understood that the definitions of the various substituents can be combined with one another in every possible and that if doing so this does not mean the introduction of new matter within the meaning of 35 U.S.P. 132.

The compounds of the invention can be prepared in different manners. Preferred processes of preparation are explained hereafter.

I. According to L. Horner (Chem. Ber. 95, p. 581 (1962)

a. the p-[1,2,4-triazolyl-(1)]-benzaldehyde (2)

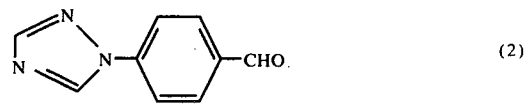

is condensed with an equimolar amount of a phosphoric compound (3)

or b. the phosphoric compound (4)

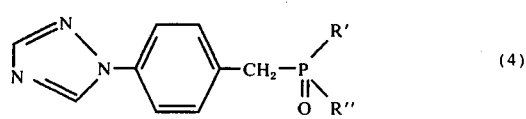

with an equimolar amount of an aldehyde (5)

OHC — A.

For the preparation of the bis-[1,2,4-triazolyl-(1)] derivatives, reactions take place between c. 2 mol of the aldehyde (2) and 1 mol of a bis-phosphone ester compound (6)

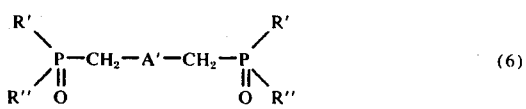

or d. 2 mol of the phosphoric compound (4) and 1 mol of a dialdehyde (7)

OHC—A'—CHO                                (7)

In the general formulae (3) and (5) A has the above indicated meaning, preferably diphenylyl-(4)-, p-carboxmethoxy-phenyl-, p-[benzoxazolyl -(2)]-phenyl-, p-[N-methyl-benzimidazolyl-(2)]-phenyl-, β-naphthyl-, β-naphthyl-, styryl-, 4-cyannaphthyl-(1)-, 4-carbomethoxy-naphthyl(1)-, 6-carbomethoxy-naphthyl-(2)-, p-carbomethoxy-styryl-, benzofuranyl-(2)-, benzoxazolyl-(2)- or 5,6-dimethylbenzoxazolyl-(2)-.

In the general formulae (6) and (7) A' stands for the radicals

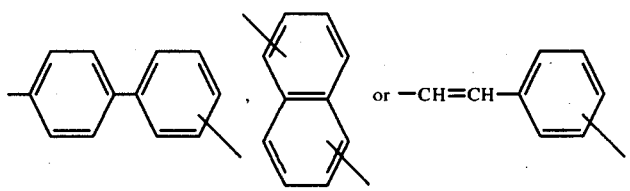

preferably for the diphenyl radical-(4,4') or for the naphthylene radical (2,6).

In the formulae (3), (4) and (6) R' and R" stand each for identical or different, alkyl-, cycloalkyl or aryl radicals eventually linked by means of an oxygen atom onto the phosphorus atom. As the radicals R' and R" do not appear in the final-product, their chemical nature is not critical in view of the final product. For practical reasons however, preference is given to cyclohexyl-, penyl- and especially to lower alkyl radicals.

The abovementioned processes are advantageously effected in indifferent solvents, for example in hydrocarbons such as, toluene or xylene or alcohols such as, methanol, ethanol, isopropanol, butanol, glycol, glycol ethers such as, 2-methoxyethanol, hexanol, cyclohexanol, cyclooctanol, furthermore in ethers such as, diisopropyl ether, dioxane, tetrahydrofurane and in formamides and N-methylpyrrolidone. Especially suitable are bipolar organic solvents such as, dimethylformamide and dimethylsulfoxide.

As condensation agents there can be used strongly basic compounds such as for example, alkaline- or earth alkaline metal hydroxides, preferably potassium hydroxide, sodium hydroxide, potassium tert. butylate or sodium methylate; furthermore the alkaline compounds of dimethylsulfoxide and alkali-hydrides.

The temperature of the reaction depends on the nature of the starting materials, and varies between 0° and about 100° C, preferably between about 10° and about 80° C.

The compounds of the invention are also obtained by using quaternary phosphonium salts, such as triphenylphosphonium salts instead of the phosphorous compounds (3), (4) and (6), condensing them according to WITTIG with the aldehydes (2), (5) and (7).

The p-[1,2,4-triazolyl-(1)]-benzaldehyde (2) which is not yet described, is prepared in the following way: p-[1,2,4-triazolyl-(1)]-benzoic-acid methyl ester is reluxed with hydrazine hydrate in n-butanol to yield the respective acid hydrazide, which forms in a reaction with benzene sulfochloride in water the phenylsulfonyl-hydrazide According to J. S. McFadyen and Th. S. Stevens (Soc. 1936, p. 584–587) that latter one is split to the aldehyde (2) by heating in glycol in the presence of sodium carbonate.

The phosphorus compound (4) can be prepared in the usual way from p-[1,2,4-triazolyl-(1)]-toluene by bromination in the side chaine with n-bromosuccinimide and by a reaction according to ARBUSOW of the bromomethyl compound with, for example, triethylphosphite.

II. Furthermore, the compounds of the invention can be prepared by condensation of p-[1,2,4-triazolyl-)1)]-benzaldehyde (2) with malonic acid, according to the process of DOEBNER-PERKIN, to the corresponding p-[1,2,4-triazolyl-(1)]-cinnamic acid, which can be converted in the usual way into the p-[1,2,4-triazolyl-(1)]-styryl-benzoxazoles, benzimidazoles or -5-phenyl-1,3,4-oxdiazoles.

Some of the compounds of the invention, substituted by heterocyclic groups in the radical A of the general formula (1), are preferably obtained by applying the HORNER-reaction to starting products (3) and (5) containing carbomethoxy-groups; the so obtained condensation products are saponified to the free acids from which, in the usual way the benzoxazolyl-(2)-, benzimidazolyl-(2)- or 5-phenyl-1,3,4-oxdiazolyl-(2) groups are built-up.

The quaternary salts of the compounds of the formula (1) are obtained in the usual way from 1,2,4-triazolyl compounds, using alkylation agents in indifferent organic solvents at elevated temperatures. As solvents can be used: chlorobenzene, o-dichlorobenzene, toluene, xylene and dimethylformamide. Reaction temperature: 50°–150° C, preferably 90°–130° C. The preferred alkylation agents are: dimethylsulfate, diethylsulfate, benzene sulfonic acid methyl ester, p-toluene sulfonic acid methyl ester, ethylbromide and n-butyl bromide.

The final products can be converted to compounds having different substituents by way of known processes, for example sulphonation with sulphonating agents, such as for example $H_2SO_4$, mixtures of $H_2SO_4$ and $SO_3$, amidosulfonic acid or chlorosulfonic acid, or conversion of sulfonic acid or carboxylic acid group to compounds with functionally modified sulfo- or carboxy groups, respectively, the conversions of such groups into others of the same kind or into the corresponding free acids.

According to the condensation process described above, and by conversion of the condensation products so obtained, the following compounds can be prepared:
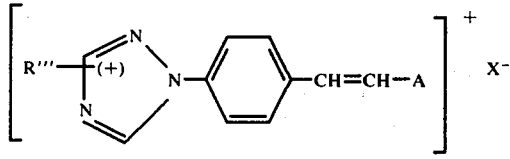
| crt.no. | R''' | A | X⁻ |
|---|---|---|---|
| (101) | H | 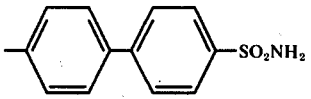 —SO$_2$NH$_2$ | Cl⁻ |
| (102) | CH$_3$ | 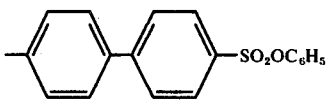 —SO$_2$OC$_6$H$_5$ | CH$_3$OSO$_3$⁻ |
| (103) | H | 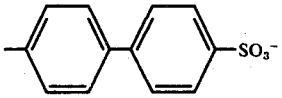 —SO$_3$⁻ | — |
| (104) | C$_2$H$_5$ | 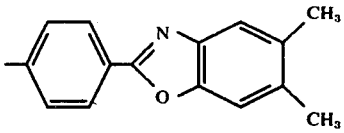 | C$_2$H$_5$OSO$_3$⁻ |
| (105) | CH$_3$ | 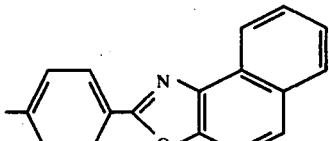 | CH$_3$OSO$_3$⁻ |
| (106) | CH$_3$ | 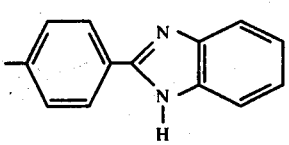 | CH$_3$OSO$_3$⁻ |
| (107) | CH$_3$ | 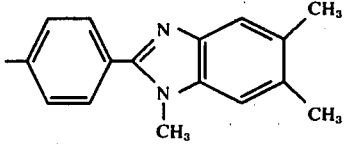 | C$_6$H$_5$SO$_3$⁻ |
| (108) | CH$_3$ | 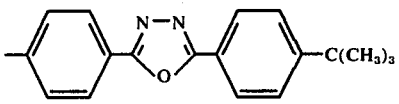 —C(CH$_3$)$_3$ | CH$_3$C$_6$H$_4$SO$_3$⁻ |
| (109) | CH$_3$ | 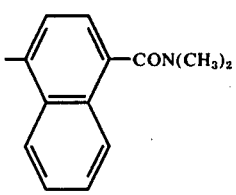 —CON(CH$_3$)$_2$ | CH$_3$OSO$_3$⁻ |

-continued

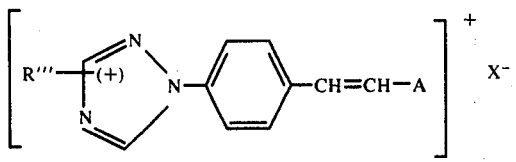

| crt.no. | R''' | A | X⁻ |
|---|---|---|---|
| (110) | CH₃ | 4-methylnaphthalen-1-yl linked to benzoxazol-2-yl | CH₃OSO₃⁻ |
| (111) | CH₃ | naphthalen-2-yl-COOCH₂CH₂N(CH₃)₂ | CH₃OSO₃⁻ |
| (112) | CH₃ | naphthalen-2-yl linked to 1-methylbenzimidazol-2-yl | CH₃OSO₃⁻ |
| (113) | CH₃ | naphthalen-2-yl linked to 5-phenyl-1,3,4-oxadiazol-2-yl | CH₃OSO₃⁻ |
| (114) | C₄H₉ | —CH=CH—C₆H₅ | Br⁻ |
| (115) | CH₃ | —CH=CH—C₆H₄—COOC₄H₉ | C₆H₅SO₃⁻ |
| (116) | CH₃ | —CH=CH—C₆H₄—CON(CH₂CH₂OH)₂ | CH₃OSO₃⁻ |
| (117) | CH₃ | —CH=CH—C₆H₄— linked to 1,5-dimethylbenzimidazol-2-yl | CH₃—C₆H₄—SO₃⁻ |
| (118) | CH₃ | 2-methyl-6-methoxybenzofuran-yl | Cl⁻ |
| (119) | CH₃ | 2,5,6-trimethylbenzofuran-yl | CH₃OSO₃⁻ |

-continued
$$\left[ R''' \underset{N}{\overset{N}{\underset{(+)}{\diagup}}} N - \underset{}{\bigcirc} - CH=CH-A \right]^{+} X^{-}$$
| crt.no. | R''' | A | X⁻ |
|---------|------|---|-----|
| (120) | CH₃ | 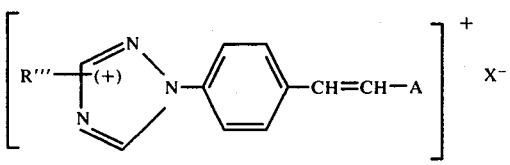 | CH₃OSO₃⁻ |
| (121) | CH₃ | 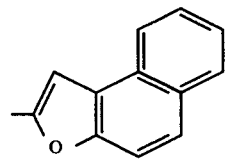 | CH₃OSO₃⁻ |
| (122) | CH₃ | 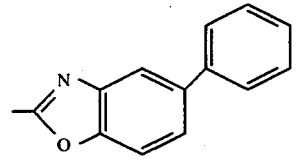 | CH₃OSO₃⁻ |
| (123) | CH₃ | 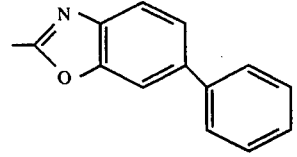 | CH₃OSO₃⁻ |
| (124) | CH₃ | 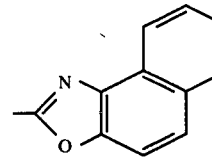 | CH₃OSO₃⁻ |
| (125) | CH₃ | 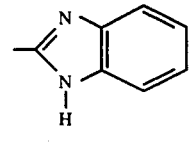 | CH₃OSO₃⁻ |
| (126) | CH₃ | 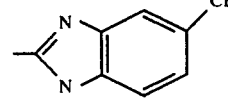 | CH₃OSO₃⁻ |
| (127) | C₂H₅ | 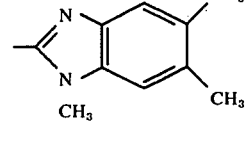 | C₂H₅OSO₃⁻ |
| (128) | CH₃ | 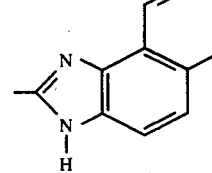 | CH₃OSO₃⁻ |

-continued

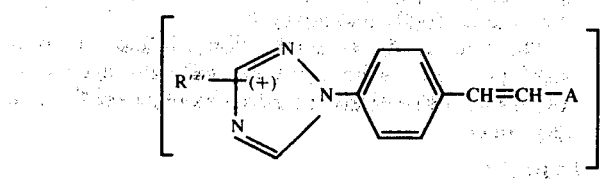

| crt.no. | R''' | A | X⁻ |
|---|---|---|---|
| (129) | CH₃ | 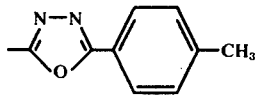 | CH₃OSO₃⁻ |
| (130) | CH₃ | 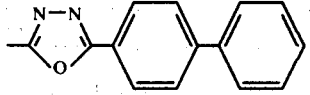 | CH₃OSO₃⁻ |
| (131) | CH₃ |  | CH₃OSO₃⁻ |

Due to their fluorescence, the new compounds of the invention have a large field of application. First of all, they are used for optical brightening of various natural and synthetic materials. These materials also include such organic materials, which can be used for the finishing of mineral substances, as for example, anorganic pigments.

As substrates to be brightened, there can be cited, for example: lacquers, synthetic fibres such as, for example those of acetylcellulose, polyamides, polyolefines, polyvinylchloride, polyvinyliden-chloride, especially polyacrylonitrile as well as foils, films, fleeces and shaped articles of such materials.

The compounds of the invention insoluble in water can be used dissolved in organic solvents or in an aqueous dispersion, preferably with the aid of a dispersing agent. As dispersing agents there can be cited, for example, soaps, polyglycol ethers which derive from fatty alcohols, fatty amines or alkylphenols, cellulose sulfite waste liquors or condensation products of eventually alkylited naphthalino-sulfonic acids with formaldehyde.

The brightening of the fibre materials with the aqueous or eventually organic brightening liquor can be effected either in an exhaust process at temperatures of preferably about 20° to 150° C, or under thermosol conditions, whereby the textile material is, for example, impregnated or sprayed with the brightening solution or dispersion and squeezed with rollers to a liquor content of about 50 to about 120 %. Subsequently, the textile material is treated for about 10 to about 300 seconds with heat, preferably with dried heat at about 120° to about 240° C. This thermosol process can also be combined with other finishing operations, for example, finishing with synthetic resins to provide an easy care property, whereby the material is eventually heated for the purpose of cross-linking for 5–20 minutes at 150–200 after the impregnation and drying at 100°–150° C.

The new compounds are in the form of solution or in dispersed form excellent brighteners with good fastness to light for fibre materials, especially those of polyacrylonitrile or polyacrylonitrile-copolymerisates, especially of copolymers common in commerce with a content of at least 85 % of acrylonitrile. Particularly high degrees of whiteness are achieved with these brighteners when they are used at temperatures between about 90° and about 130° C, preferably between about 95° and about 105° C, in the presence of oxydative bleaching agents such as, for example sodium chlorite. It has prooved that it is particularly advantageous, when the products of the invention are utilized under the before-mentioned conditions in an acid pH range of about pH 2 and about pH 5. A special advantage of the products of the invention is, that brightening effects are almost not influenced by changes in the pH value within the before-mentioned range. Preference is given in this case to compounds which do not contain acid groups, especially in form of salts, such as quaternary salts. Especially due to the insensibility in respect of the pH, the new products are superior to the products which are actually used in this field of application.

The compounds of the general formula (1) can also be added to detergents. They can contain the usual fillers and auxiliaries such as alkali silicates, alkali phosphates or condensed phosphates, alkaliborates, alkali salts of carboxymethylcellulose, foam stabilisators, such as alkanolamides of higher fatty acids or complex builders, such as soluble salts of the ethylendiaminotetraacetic acid or of diethylentriaminopenta acetic acid, as well as chemical bleaching agents such as perborates or percarbonates, perborate activators of the type of polyacetic acid amides, which, in connection with peroxides lead to the split-off of the per-acetic acid, and disinfection agents.

Furthermore, the compounds of the invention can be added to high-molecular organic materials before or during their straping.

It is, for example, possible to add them to the presscake in the course of the preparation of fibres, films, foils, ribbons and shaped articles, or to dissolve them before spinning in the spinning mass. Suitable compounds can also be added to lower molecular starting materials before polycondensation or polymerisation, as in the case of polyamide-6, polyamide-6,6 or polyacryl-nitrile.

The quantity of the compounds of the invention of the general formula (1), related to the material to be optically brightened, can considerably vary depending on the field of application and the requested effect. It can easily be found by tests and ranges generally between about 0.01 and about 1 %.

The compounds of the invention can furthermore be used in mixture with dyestuffs, softening agents and especially with cationic after-treatment agents for laundry goods.

TABLE 1

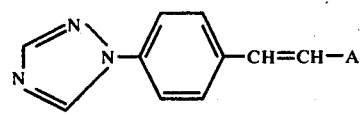

| Crt. no. | A | Melting point °C | Absorption*) λ max [n m] | $\epsilon \cdot 10^{-4}$ |
|---|---|---|---|---|
| (201) | | 267–269 | 342 | 5,53 |
| (202) | | 272–273 | 358 | 6,59 |
| (203) | | 213–215 | 343 | 5,69 |
| (204) | | 275 u.Zers | 337 | 4,84 |
| (205) | | 327–330 | 357 | 6,15 |
| (206) | | 209–211 | 354 | 6,53 |
| (207) | | 183–184 | 338 | 2,95 |
| (208) | | 180–181 | 358 | 2,97 |

TABLE 1-continued
| | | | | |
|---|---|---|---|---|
| (209) | 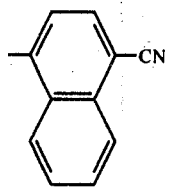 | 241–243 | 362 | 3,35 |
| (210) | 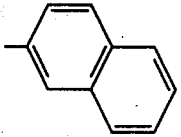 | 207–209 | 335 | 4,92 |
| (211) | 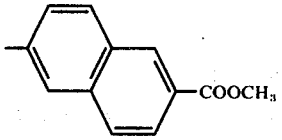 | 235–236 | 348 | 5,28 |
| (212) | 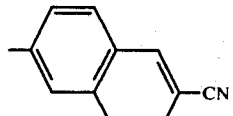 | 217–218 | 348 | 5,23 |
| (213) | 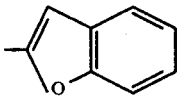 | 202–204 | 350 | 5,28 |
| (214) | 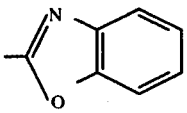 | 274–276 | 336 | 4,54 |
| (215) | 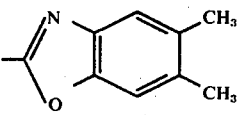 | 266–268 | 343 | 4,25 |
| (216) | 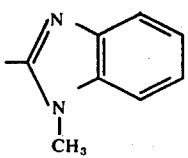 | 263–265 | 348 | 3,94 |
| (217) | 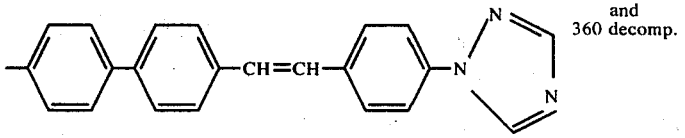 | and 360 decomp. | 367 | 9,11 |
| (218) | 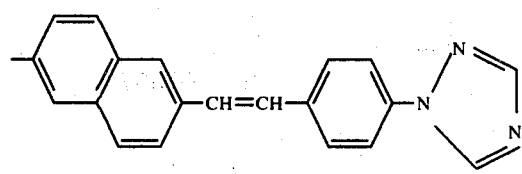 | and 357 decomp. | 364 | — |
*) measured in dimethylformamide

TABLE 2
$$\left[ R'''\underset{N}{\overset{N=N}{\diagdown\diagup}}(+)\underset{}{}N-\bigcirc\!\!\!\!\!\!\!\!\!\!\!-CH=CH-A \right]^{+} X^{-}$$
| Crt. no. | A | R''' | X⁻ | Absorption* max [nm] | $\epsilon 10^{-4}$ |
|---|---|---|---|---|---|
| (301) | 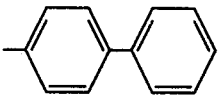 | CH₃ | CH₃OSO₃⁻ | 338 | 4,72 |
| (302) | 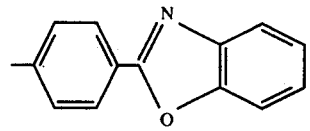 | CH₃ | CH₃OSO₃⁻ | 356 | 5,78 |
| (303) | 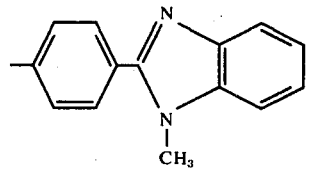 | CH₃ | CH₃OSO₃⁻ | 338 | 5,11 |
| (304) | 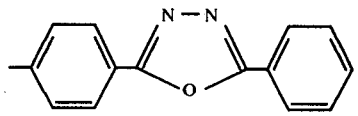 | CH₃ | CH₃OSO₃⁻ | 342 | 4,27 |
| (305) | 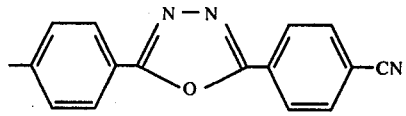 | CH₃ | CH₃OSO₃⁻ | 356 | 5,49 |
| (306) | 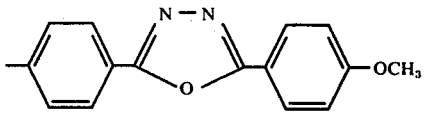 | CH₃ | CH₃OSO₃⁻ | 347 | 4,11 |
| (307) | 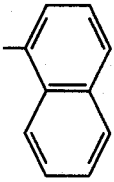 | CH₃ | CH₃OSO₃⁻ | 340 | 2,48 |
| (308) | 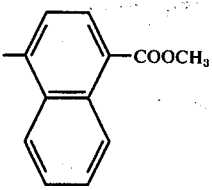 | CH₃ | CH₃OSO₃⁻ | 362 | 2,84 |
| (309) | 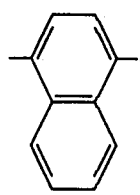 | CH₃ | CH₃OSO₃⁻ | 360 | 2,91 |

TABLE 2-continued $$\left[ R''' \underset{N}{\overset{N}{\underset{(+)}{\bigtriangleup}}} N-\underset{}{\bigcirc}-CH=CH-A \right]^{+} X^{-}$$

| Crt. no. | A | R''' | X⁻ | Absorption*) max [n m] | $\epsilon 10^{-4}$ |
|---|---|---|---|---|---|
| (310) | naphthyl | CH₃ | CH₃OSO₃⁻ | 333 | 3,93 |
| (311) | naphthyl-COOCH₃ | CH₃ | CH₃OSO₃⁻ | 353 | 5,13 |
| (312) | naphthyl-CN | CH₃ | CH₃OSO₃⁻ | 348 | 5,23 |
| (313) | benzofuran | CH₃ | CH₃OSO₃⁻ | 351 | 4,17 |
| (314) | benzoxazole | CH₃ | CH₃OSO₃⁻ | 340 | 2,80 |
| (315) | 5,6-dimethylbenzoxazole | CH₃ | CH₃OSO₃⁻ | 349 | 2,24 |
| (316) | 1-methylbenzimidazole | CH₃ | CH₃OSO₃⁻ | 343 | 2,87 |
| (317) | biphenyl-CH=CH-C₆H₄-N(+)-imidazolyl(CH₃) CH₃OSO₃⁻ | CH₃ | CH₃OSO₃⁻ | — | — |

TABLE 2-continued

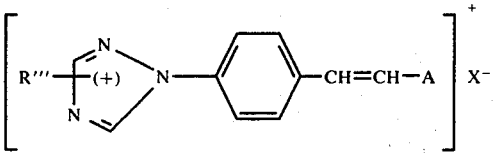

| Crt. no. | A | R''' | X⁻ | Absorption*) max [n m] | ε10⁻⁴ |
|---|---|---|---|---|---|
| (318) | (naphthyl-CH=CH-C₆H₄-N(+)-triazole-CH₃ structure) CH₃OSO₃⁻ | CH₃ | CH₃OSO₃⁻ | 377 | 6,9 |

*)measured in dimethylformamide

EXAMPLES FOR THE PREPARATION

Example 1

5.2 g of -[1,2,4 triazolyl-(1)]-benzaldehyde (2) and 11.1 g of diphenyl-(4)-methyldiethylphosphonate (content according to gas chromatographic analysis- hereafter GC at 82.4 %) were dissolved in 30 ml of dimethyl-formamide and added dropwise in about 10 minutes to a solution of 4.24 g of potassium tert. butylate in 60 ml of dimethylformamide. The temperature raises hereby from 20° to 50° C. Subsequently it was stirred for 30 minutes without cooling and the mixture was then poured into 500 ml of water; the pH value was then adjusted with diluted hydrochloric acid to pH 8–9. The precipitated product was suction-filtered, washed with water until free from Cl ions and dried in vacuo at 60° C. 9.69 g of the crude 4-[1,2,4-triazolyl-(1)]-4'-phenyl-stilbene (201) were obtained as bright yellow powder which melted after re-dissolution from chlorobenzene at 267°–269° C.

Example 2

5.2 g of p-[1,2,4-triazolyl-(1)]-benzaldehyde (2) and 8.2 g of benzo-furanyl-(2)-methyl-diethylphosphonate (content GC 98.1 %) were dissolved in 30 ml of dimethylformamide and added within about 10 minutes at 20° to 45° C to a solution of 4.24 g of potassium-tert.-butylate in 60 ml of dimethylformamide. The clear brown solution was stirred during 1 hour, poured onto 500 ml of water and adjusted to pH 8 with diluted hydrochloric acid. Suction-filtering followed and it was washed with water until free from Cl ions and dried in vacuo at 60° C. 8.54 g of 2-[p-(1,2,4-triazolyl-(1)styryl]-benzofurane (213) were obtained as yellow powder which melted after re-dissolution from n-butanol at 202°–204° C.

The p-[1,2,4-triazolyl-(1)]-benzaldehyde used in examples 1 and 2 was obtained in the following way: 81.2 g of p-[1,2,4-triazolyl-(1)]-benzoic acid methyl ester were suspended in 480 ml of n-butanol and 50 g of hydrazinhydrate (80 %) were added. It was heated until boiling whilst stirring and refluxed during 54 hours. After cooling to 0°–5° C, the product was suction-filtered, washed with butanol and water and dried at 60° C in vacuo. 73 g of a brownish powder was obtained, which melted under decomposition at 324° C. 203 g of this hydrazide were supended in 1 l of water, 141 ml of benzenesulfochloride were added and kept at 60° C. By addition of 385 ml of a solution of 4 N sodiumcarbonate, the pH value was adjusted to 6–7. When acid is no longer developed, stirring is continued during 30 minutes at about 60° C, the mixture cooled to room-temperature, suction-filtered and washed with water until free from Cl ions. After drying in vacuo at 60° C, 304 g of a brownish powder with a decomposition point of 207° C were obtained. 68.7 g of this benzenesulfonyl-hydrazide were mixed with the same quantity of water-free sodiumcarbonate and added, whilst stirring at room temperature, to 400 ml of glycol. The mixture was heated in about 10 minutes to 90°–135° C, whereby a violent gas development occurred. Immediately afterwards it was poured onto 600 ml of water and the temperature was raised to 95° C. After a short stirring it was suction-filtered at this temperature and the filtrate was cooled. The crystallized product was suction-filtered, washed with water and dried in vacuo at 60° C. 12.7 g. of p-[1,2,4-triazolyl-(1)]-benzaldehyde (2) with a melting point of 144°–146° C were obtained. By extraction of the aqueous mother liquor with methylenchloride, it is still possible to obtain about 5 g of the aldehyde.

Example 3

The p-[1,2,4-triazolyl-(1)]-benzyl-diethylphosphonate is prepared in the following way: 51.6 g of p-[1,2,4-triazolyl-(1)]-toluene were dissolved in 320 ml of tetra-chlorocarbon and added to 57.6 g of N-bromosuccinamide and 0.32 g of azo-iso-butyric acid-dinitrile and heated during two and a half hours under UV radiation until ebullition. The precipitated succinimide was then suction filtered and the filtrate was evaporated. Out of residue from evaporation, 26 g of p-[1,2,4-triazolyl-(1)]-benzyl-bromide with a melting point of 98°–99° C were obtained by re-dissolution from ethanol. 23.8 g of this bromide compound were suspended in 50 ml of triethylphosphite, heated whilst stirring up to an internal temperature of 130° C and kept at this temperature for 6 hours, whereby the compound dissolved slowly. The triethylphosphite in excess was distilled off in vacuo and the content of the remaining oleogenous p-[1,2,4-triazolyl-(1)] benzyldiethyl-phosphonate is determined by gas chromatography.

Example 4

The 4-[1,2,4-triazolyl-(1)]-4'-carbomethoxystilbene with a melting point of 208°–210° C, prepared according to example 1, was saponified in the following way: 54.7 g of the methyl ester were suspended in 1.5 l of ethanol and added to a solution of 10.8 g of sodium hydroxide in 20 ml of water. It was refluxed during 1 hour and the ethanol was then distilled off whilst 2 l of water were slowly added. 30 ml of concentrated hydrochloric acid were introduced into the hot solution of which the Na salt of the acid precipitated already and stirred during 1 hour at 90°–95° C. The mixture was cooled to 10° C, the precipitated acid was suction-filtered and washed with water until free from Cl ions. After drying at 60° C in vacuo, 52 g of 4-[1,2,4-triazolyl-(1)]-4'-carboxystilbene with a decomposition point of 338° C were obtained.

Example 5

25.0 g of malonic acid were dissolved in 36 ml of pyridine and added after cooling to room temperature to 34.6 p-[1,2,4-triazolyl-(1)]-benzaldehyde(2) and 1.97 ml of pyridine. The mixture was slowly heated to 90°–95° C and was kept at this temperature until the end of gas formation. The preparation was then put onto a mixture composed of 300 ml of ice/water and 50 ml of hydrochloric acid, it was stirred for 15 minutes, suction-filtered, washed with water until free from Cl ions and dried in vacuo at 60° C. 39 g of 4-[1,2,4-triazolyl-(1)]-cinnamic acid with a point of decomposition of 297° C were obtained.

Example 6

14.5 g of 4-triazolyl-(1)]-4'-carboxy-stilbene (example 4) were suspended in 200 ml of chlorobenzene at room temperature; 2 drops of dimethylformamide and 4.39 ml of thionylchloride were added and the whole was stirred for 5 hours at 70°–80° C. Chlorobenzene and thionyl-chloride were then distilled off in water jet vacuum, the residue was then added to 200 ml of o-dichlorobenzene and thoroughly stirred. 9.76 of o-phenylene-diamine-hydrochloride were added and in the course of 1 hour the mixture was brought to a temperature of 175° C. This temperature was kept for 30 minutes; the mixture was then cooled to room temperature, 100 ml of a concentrated ammonia solution were added and the whole was vigorously stirred for 30 minutes. The o-dichlorobenzene was eliminated with steam and the remaining aqueous phase was cooled and suction-filtered. The suction-filtered product was washed with water until free from Cl ions and dried in vacuo at 60° C. 18.3 g of the crude 4-[1,2,4-triazolyl-(1)]-4'-[N-methyl-benzimidazolyl-(2)]-stilbene (203) were obtained as bright yellow powder which melts at 213°–215° C after redissolution from n-butanol.

Example 7

7,46 g of 4-[1,2,4-triazolyl-(1)]-4'-carboxy-stilbene (example 4) were converted into the acid chloride in 100 ml of chlorobenzene with 2,2 ml of thionylchloride (as indicated in example 6). The residue of the distillation was put into 80 ml of chlorobenzene and mixed at 80° C with 3,41 g of benzoic acid hydrazide and 6,7 ml of N,N-dimethyl-aniline. It was refluxed during 5 hours, cooled to 5° C and the precipitated product was isolated on a suction filter. The suction-filtered product was washed with methanol and water and dried in vacuo at 60° C. 10,18 g of benzylhydrazide was obtained as a brownish powder. This powder was suspended in 200 ml of phosphoroxychloride and stirred under refluxing during 7 hours. The phosphoroxychloride was then distilled off in vacuo, the residue was then mixed with 200 ml of water and the whole was thoroughly stirred. The pH value was adjusted to pH 9 with a small quantity of concentrated caustic soda solution, heated for a short time to 90° C and suction-filtered after cooling to 40° C. The suction filtered product was then washed with water until from Cl ions and dried in vacuo at 60° C. 9.53 g of the crude 4-]1,2,4triazolyl-(1)]-(1)-4'-[5-phenyl-1,3,4- oxidiazolyl-(2)]-silbene was obtained in form of a bright yellow powder which melted under decomposition at 275° C after re-dissolution from dimethylformamide.

Example 8

14.5 g of 4-[1,2,4-triazolyl-(1)[-4'-carboxy-stilbene (example 4) were converted into the acid chloride as indicated in example 6. The residue of the distillation was put into 250 ml of chlorobenzene, added to 5,46 g of aminophenol and 13 g of N,N-dimethylaniline and stirred during 5,5 hours at 70°–90° C. The mixture was cooled to 10° C and the precipitated product was suction filtered, washed with methynol and water until free from Cl ions and dried in vacuo at 60° C. 19 g of the acylamino compound was obtained as a bright yellow powder with a melting point of 298°–300° C. 17,2 g of this product were suspended at room temperature in 150 ml of 1,2,4-trichlorobenzene, 0,8 g of p-toluene sulfonic acid were added and the solution was stirred under adduction of nitrogen for 1 hour at 205°–210° C. A clear green solution was obtained. About 100 ml of the solvent were distilled off in vacuo, the residue was added at room temperature to 100 ml of a concentrated ammonia solution and stirred during 30 minutes. The remaining trichlorobenzene was distilled off with steam, the reaction product contained in the aqueous phase was suction-filtered, washed with methanol and water and dried in vacuo at 60° C. 14.4 g of the crude 4-[1,2,4-triazolyl-(1)]-4'-[benzo-xyzolyl-(2)]-stilbene (202) were obtained as yellow powder which melted after re-dissolution from dimethylformamide at 272°–273° C.

Example 9

19.35 g of the cyano-naphthyl compound (209) were dissolved under stirring in 1 l of chlorobenzene and added to 6 ml of dimethylsulfate. The mixture was refluxed during 6 hours, cooled to room temperature and suction filtered. The suction-filtered product was washed with benzene and dried in vacuo at 60° C. 25,4 g of the triazolium compound (309) were obtained which dissolves clearly in warm water.

Example 10

100 g of a polyarylnitrile fabric common in commerce were treated in a liquor of the following composition:

1,2 g/l of sodium chlorite (50 %)
0,5 g/l of a bleaching agent common in commerce (based on a long-chained alkylsulfonate)
0,2 g/l of acetic acid (100 %) sulfuric acid up to pH 3,5 to pH$_2$
0,075 g/l of the compound (313)
Liquor ratio: 1 : 20.

The goods were put into the bath at 50° C; the temperature of the bath was then raised to 85° C within 10 minutes. At this temperature, the goods were bleached during 30 minutes, the temperature raised to boiling and treated during 45 minutes. Compared with the untreated material the fabric presented a high degree of whiteness.

The same results are obtained with the compounds (203), (309) and (308).

Example 11

30 kg of polyacrylnitrile yarn were treated in a commonly used dyeing apparatus with 0,15 % of the compounds indicated in example 10. Liquor ratio 1:40. The pH value of the liquor was adjusted to pH 4 or pH 2 (oxaluric acid).

The liquor was brought within 30 minutes from 50° C to ebullition temperature; the goods were then treated at this temperature during 30 minutes. Finally, rinsing and drying took place as usual.

The so treated yarn presented, compared with the untreated material, a high whiteness degree.

Example 12

Cationic laundry softeners were prepared with the aid of the compounds (308), (309) and (313).

0,2 g of optical brighteners and 2 g of ammonia acetate were pre-dissolved in 87,8 g of hot water and added whilst stirring to a molten mass composed of 8 g of distearyl-dimethyl-ammonium chloride and 2 g of stearine-acid polyglycol ester (with 7 ethyleneoxide parts on average).

In each case, 5 g/l of these starting mixtures were used. 100 g of a cotton fabric was washed in a liquor ratio 1 : 15 and a temperature of 25°–30° C. After this treatment, the wet goods were centrifuged and dried in the usual way. Compared with the untreated goods, the so treated material presented high whiteness effects.

We claim:

1. A compound of the formula

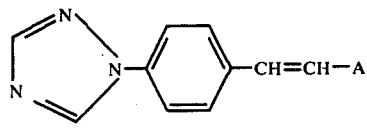

and the corresponding lower alkyl quaternary salt thereof wherein A is a group of the formula

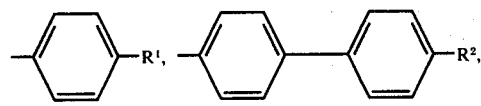

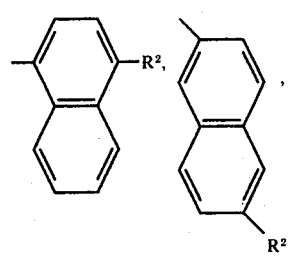

-continued

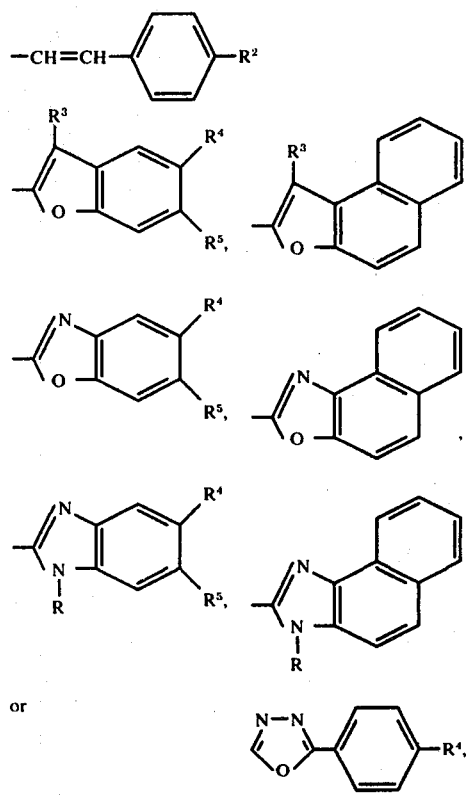

or

R is hydrogen or lower alkyl, $R^1$ is a group of the formula

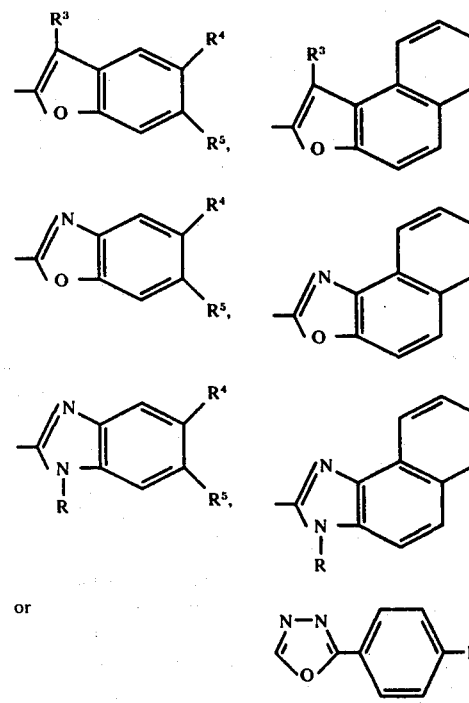

or $R^3$ is hydrogen or lower alkyl, $R^4$ and $R^5$ are hydrogen, cyano, lower alkyl, lower alkoxy or phenyl, carbo lower alkoxy, lower alkanoylamino and $R^2$ is hydrogen, sulfonamido, sulfonic acid, sulfonic acid lower alkyl ester, di lower alkyl carbonamido di lower alkyl-amino lower alkyl carbonamido, di hydroxy lower alkyl carbonamido, carbo lower alkoxy, cyano, or a group of the formulae

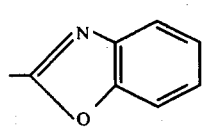

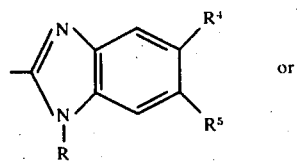 or

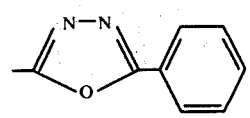

2. A compound as claimed in claim 1, in the form of its methyl quaternary methosulfate salt wherein A is

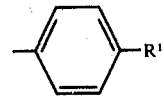

and R¹ is

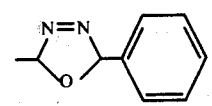

3. A compound as claimed in claim 1, in the form of its methyl quaternary methosulfate salt wherein A is

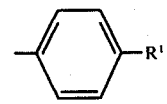

and R¹ is

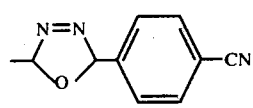

4. A compound as claimed in claim 1, in the form of its methyl quaternary methosulfate salt wherein A is

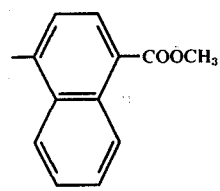

5. A compound as claimed in claim 1, in the form of its methyl quaternary methosulfate salt wherein A is

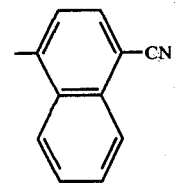

6. A compound as claimed in claim 1, in the form of its methyl quaternary methosulfate salt wherein A is

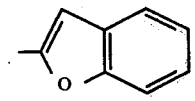

* * * * *